United States Patent [19]

McAlister

[11] Patent Number: 4,692,537
[45] Date of Patent: Sep. 8, 1987

[54] ORGANOSILICON COMPOUNDS

[76] Inventor: Roy E. McAlister, 5285 Red Rock North, Phoenix, Ariz. 85018

[21] Appl. No.: 810,307

[22] PCT Filed: Apr. 9, 1984

[86] PCT No.: PCT/US84/00521
§ 371 Date: Dec. 9, 1985
§ 102(e) Date: Dec. 9, 1985

[87] PCT Pub. No.: WO85/04660
PCT Pub. Date: Oct. 24, 1985

Related U.S. Application Data

[63] Continuation-in-part of Ser. No. 312,073, Oct. 16, 1981, Pat. No. 4,458,087.

[51] Int. Cl.$^4$ .............................. C07F 7/08; C07F 7/18
[52] U.S. Cl. .................... 556/484; 556/465; 556/488; 556/485; 526/242; 526/249; 528/25
[58] Field of Search ............... 556/465, 488, 485, 484; 526/242, 249; 528/25

[56] References Cited

U.S. PATENT DOCUMENTS

| | | | |
|---|---|---|---|
| 2,539,638 | 1/1951 | Schilling | 23/108 |
| 2,675,307 | 1/1954 | Klugh | 75/29 |
| 2,682,512 | 6/1952 | Agre | 556/488 X |
| 2,800,494 | 7/1957 | Haluska | 556/488 X |
| 2,802,851 | 8/1957 | Moore | 556/488 X |
| 2,962,357 | 11/1960 | Williams | 23/165 |
| 3,453,079 | 7/1969 | Langer | 23/203 |
| 3,661,519 | 5/1972 | Driscoll | 23/182 |

FOREIGN PATENT DOCUMENTS 0059284 12/1967 German Democratic Rep. .................. 556/488

OTHER PUBLICATIONS

"Angewandte Chemie Int. Ed.", 5, No. 12, (1966), pp. 1023–1027.
Tarbutton, "Ind. Eng. Chem.", 50, (1958), pp. 1525–1528.

Primary Examiner—Paul F. Shaver
Attorney, Agent, or Firm—Cushman, Darby & Cushman

[57] ABSTRACT

There are prepared silafluoroolefins and silafluoroolefin ethers and polymers thereof by reacting carbon with silicon tetrafluoroide and a source of hydrogen followed by polymerization. The polymers are useful for architectural purposes and as release coatings.

11 Claims, 5 Drawing Figures

Fig. 1.

ORGANOSILICON COMPOUNDS

BACKGROUND OF THE INVENTION

A well-known waste product of the phosphate fertilizer industry is silicon tetrafluoride. Silicon tetrafluoride in this context is a gaseous by-product of common phosphate rock and acid reactions that are used to produce soil fertilizers. The most common phosphate rock used as a source mineral for production of soil fertilizers contains, on a dry weight basis, appreciable portions of fluoroapatite $Ca_{10}F_2(PO_4)_6$ and silica $SiO_2$. Upon reaction with acids such as phosphoric or sulfuric acid, silicon tetrafluoride is released:

$$SiO_2 + Ca_{10}F_2(PO_4)_6 + H_2SO_4 \rightarrow CaH_4(PO_4)_2 + Ca(SO_4).H_2) + SiF_4$$

The silicon tetrafluoride released is generally accompanied by hydrogen fluoride, water vapor, gaseous oxides of sulfur and nitrogen. As noted in Table 1, the major U.S. deposits of phosphate rock contain $SiO_2$ and F and the average yield of fluorine is about 230 lbs per ton of fertilizer produced.

TABLE 1

| Location and Type | REPRESENTATIVE ANALYSES OF COMMERCIAL PHOSPHATE ROCKS | | | | | | | | | | | | | |
|---|---|---|---|---|---|---|---|---|---|---|---|---|---|---|
| | $P_2O_6$ | CaO | MgO | $AL_{202}$ | $Fe_{202}$ | $SiO_2$ | $SO_2$ | F | Cl | $CO_2$ | Organic carbon | $Na_2O$ | $K_2O$ | $H_2O^a$ |
| United States | | | | | | | | | | | | | | |
| Florida | | | | | | | | | | | | | | |
| land pebble, high grade | 35.5 | 48.8 | 0.04 | 0.9 | 0.7 | 6.4 | 2.4 | 4.0 | 0.01 | 1.7 | 0.3 | 0.07 | 0.09 | 1.8 |
| land pebble, furnace grade | 30.5 | 46.0 | 0.4 | 1.5 | 1.9 | 8.7 | 2.6 | 3.7 | 0.01 | 4.0 | 0.5 | 0.1 | 0.1 | 2.0 |
| hard rock, high grade | 35.3 | 50.2 | 0.03 | 1.2 | 0.9 | 4.3 | 0.1 | 3.8 | 0.005 | 2.8 | 0.3 | 0.4 | 0.3 | 2.0 |
| hard rock, waste pond | 23.0 | 28.5 | 0.4 | 14.8 | 2.9 | 19.8 | 0.01 | 2.1 | 0.005 | 1.4 | 0.3 | 0.1 | 0.4 | 7.0 |
| Tennessee | | | | | | | | | | | | | | |
| brown rock, high grade | 34.4 | 49.2 | 0.02 | 1.2 | 2.5 | 5.9 | 0.7 | 3.8 | 0.01 | 2.0 | 0.2 | 0.2 | 0.3 | 1.4 |
| brown rock, furnace grade | 21.2 | 29.1 | 0.6 | 10.0 | 6.2 | 25.6 | 0.4 | 2.2 | | 1.2 | 0.3 | 0.3 | 0.4 | 2.5 |
| Western States | | | | | | | | | | | | | | |
| phosphoria rock, high grade | 32.2 | 46.0 | 0.2 | 1.0 | 0.8 | 7.5 | 1.7 | 3.4 | 0.02 | 2.1 | 1.8 | 0.5 | 0.4 | 2.5 |
| phosphoria rock, low grade | 19.0 | 23.3 | 1.4 | 5.9 | 4.0 | 27.4 | 1.9 | 1.8 | | 4.0 | 5.0 | 1.5 | 1.0 | 3.5 |

Table 2 shows the resulting fluorine yields for various annual consumption rates.

TABLE 2

FLUORINE SUPPLIES FROM PHOSPHATE ROCK MINERALS

| Location | Estimated Reserves (Long Tons) | Average Fertilizer Production Long Tons/Yr. | Estimated Fluorine Release Long Tons/Yr. |
|---|---|---|---|
| United States | $14 \times 10^9$ | $20 \times 10^6$ | 600,000 |
| North Africa | $25 \times 10^9$ | $13 \times 10^6$ | 390,000 |
| U.S.S.R. | $8 \times 10^9$ | $9 \times 10^6$ | 270,000 |
| Oceania | $0.2 \times 10^9$ | $2.3 \times 10^6$ | 69,000 |
| Brazil | $0.6 \times 10^9$ | $0.6 \times 10^6$ | 18,000 |
| U.A.R. | $0.2 \times 10^9$ | $0.6 \times 10^6$ | 18,000 |
| All Other | $0.7 \times 10^9$ | $4.5 \times 10^6$ | 135,000 |
| TOTALS | $48.7 \times 10^9$ | $50 \times 10^6$ | $1.5 \times 10^6$ |

Another emerging source of fluorine is in the recovery of oil from shale or dolamite reserves. Fluorine available in petrorock minerals is considered a bothersome interferace to oil recovery operations. The present invention contemplates using the hydrocarbon and fluorine constituents of petrorock minerals to form useful precursors for th production of architectural polymers. The present invention also contemplates apparatus used in the production of such architectural polymers.

The subject invention concerns recovery of the fluorine and conversion to new and useful polymers and feedstocks by novel coal or petrorock gasification process and apparatus. This invention overcomes the major problems that have defeated past efforts to economically recover fluorine from phosphate fertilizer waste streams. The problems as set out in detail in pages 1525–1528 of Ind. Eng. Chem. 50, (1958) by G. Tarbutton, T. O. Farr, T. M. Jones, and H. T. Lewis Jr., include the fact that the greatest percentage of fluorine values are set out as silicon tetrafluoride. The chemical stability of silicon tetrafluoride, based upon the high free energy of formation is sufficient to make it difficult to convert the fluorine present to hydrogen fluoride, and although several flow charts for this conversion have been tested they are not economically viable. Among the objects of the present invention are the following:

1. To develop a valuable by-product of the phosphate fertilizer industry.
2. To avoid contamination of the atmosphere by fluorine compounds that destroy ozone.
3. To develop petrorock and coal gasification treatments to provide useful products.
4. To provide a new method for extracting a desired monomer from several chemical species.
5. To provide new thermoplastic polymers having improved chemical and physical properties.
6. To provide apparatus for accomplishing the aforesaid methods which is effective in operation and economical to manufacture and maintain.

SUMMARY OF THE INVENTION

Silicon tetrafluoride is mixed with natural gas and added to a packed column of heated coal. (Recycled gas can be used in place of or in addition to natural gas.)

In place of reacting with methane and carbon the silicon tetrafluoride can be reacted with carbon alone or silicon tetrafluoride can react with ethylenically unsaturated hydrocarbons and halohydrocarbons in the presence or absence of carbon. Other possible reactions will be set forth below. Usually a mixture of products will result.

When silicon tetrafluoride reacts with carbon the product is

(I)

This is a gas which can be cooled below room temperature to form an amber colored liquid. The coloration is believed to be due to small amounts of impurities which are present.

When silicon tetrafluoride reacts with methane and carbon the major product is a mixture of (II)

and (III)

However, in the reaction there are produced a mixture of novel products of the formulae

(V)

and

(V)

where X is hydrogen or fluorine and wherein there are present 1 to 6 fluorine atoms in the molecule. The predominant amount of compounds have four fluorine atoms and usually two of the fluorine atoms are attached to the silicon atom and two to an adjacent carbon atom. The products are gases which can be condensed below room temperature to amber colored liquids. The amber color is believed to be due to the presence of small amounts of impurities.

Due to decomposition of the methane there are also formed compounds of the formulae VI and VII which have 5, 7 or 9 carbon atoms or even of the formula (VI)

and (VII)

where n is an integer of preferably 1, 2 or 3 and X is as defined above with the proviso that at least one X is fluorine.

The compounds of formulae IV and V which contain four fluorine atoms are collectively called monosilatetrafluorobutylene and the compound of Formula I can be named monosilatetrafluoroethylene.

If in addition to employing coal or other forms of carbon there is also reacted oxygen with the silicon tetrafluoride there are formed perfluorosilyl perfluoroalkylene either the formula (VIII)

and (IX)

where n is 0 or 1.

The compounds of formula VIII and IX are formed simultaneously and the perfluorovinyl perfluorosilyl ether ($C_2SIOF_6$) can be separated from the $C_3SiOF_8$ monomers by control of the condensation. The perfluorovinyl perfluorosilyl ether is more volatile than the $C_3SiOF_8$ compound.

The $C_2SiOF_6$ was separated from the $C_3SiOF_8$ compounds in the following manner. After the reaction of the silicon fluoride, carbon and oxygen at high temperature, e.g. about 1500° F. (816° C.) liquid nitrogen was used as a coolant in condensing the gaseous products. By exhaust valve control of the condenser cuts were made as a function of the liquid nitrogen flow into the condenser which was a spiral wound heat sink condense. The $C_3SiOF_8$ compounds were less volatile then the $C_2SiOF_6$ (i.e. they were higher boiling). Thus they were condensed first. By increasing the nitrogen flow there was then condensed the $C_2SiOF_6$. The more volatile products of the reaction, e.g. unreacted $SIF_4$, $H_2$, $CF_4$ and $CO$ were not condensed and were discarded.

The formula of the new monomers obtained in the condensation was determined by mass spectrometry and corroborately by emission activation.

The monomeric compounds of the invention are gases. They can be used as propellants in aerosols. They can also be used as fire extinguishers. This is especially true of the perfluoro compounds. The monomeric compounds of the invention can be polymerized by conventional techniques, e.g. by using chromic oxide, chromic chloride catalyst at elevated temperature or similarly using aluminum chloride, titanium tetrachloride or transition metal chlorides, fluorides and bromides or by using free radical catalysts, e.g. peroxides such as benzoyl peroxide, diisopropyl peroxydicarbonate, etc.

The polymers can also be prepared by the use of Natta-Ziegler catalysts using conventional Natta-Ziegler polymerization techniques and they can also be prepared by conventional aqueous emulsion and dispersion techniques.

Another polymerization procedure is to use a Natta-Ziegler type catalyst (e.g. triethylaluminum plus titanium trichloride) in a heat sink solvent, e.g. hexane to obtain good yields of the polymer.

Polymers of compounds of formulae I through IX are used for architectural purposes. Thus they can be used to make wear resistant tubing, solar panels or films on aluminum or other metals by extrusion. The polymers are useful as roofing siding panels. The polymers in the form of films can be used for packaging. Furthermore they can be used as release coatings, e.g. on molds.

The monomers of formulae I through IX can also be copolymerized with each other and with other monomers, e.g. ethylene, propylene, vinyl chloride, vinylidene chloride, tetrafluoroethylene, perfluoropropylene, chlorotrifluoroethylene, vinyl fluoride or vinylidene fluoride, to give copolymers with similar uses.

The reaction of the silicon tetrafluoride with carbon can take place for example at 1800° F. to form monosilatetrafluoroethylene. This compound can then be reacted with methane or ethylene at 1200°–1500° F. to form monosilatetrafluorobutylene. Alternatively the latter material can be prepared by mixing together all of the reactants.

To separate monosilatetrafluorobutadiene from more volatile gases the gaseous mixture can be cooled until the monosilatetrafluorobutylene condenses as a liquid. The liquid can then be distilled to purify it by leaving less volatile materials behind. The monosilatetrafluoroethylene can be purified in similar manner.

The monosilatetrafluorobutylene monomer is also identified below on occasion as ESCTF since it can be considered to have an ethylene silicon carbide tetrafluoride structure. Thus methane and carbon can react to form ethylene which in turn reacts with SiCF$_4$.

In the following description the equations are not necessarily balanced but are presented to indicate the types of reactants and products.

When silicon tetrafluoride is mixed with natural gas and added to a packed column of heated coal the primary reaction involving the silicon tetrafluoride can be represented as follows.

$$SiF_4 + CH_4 + C \longrightarrow \text{EQUATION 1}$$

Methane gas, carbon supplied by the coal, and silicon tetrafluoride are bonded in an ethylene silicon carbide tetrafluoride structure, ("ESCTF"). This new monomer may be polymerized to suitable molecular weights by conventional polymerizing techniques for developing highly desirable thermoplastic characteristics. Chain growth polymerization by homogeneous initiation or heterogeneous initiation on solid catalysts with the new monomer is analogous to chain growth with $CH_2=CH_2$ and $CH_2=CH_2+CF_2-CF_2$ and there can be used the polymerization procedures employed with such monomers.

In another embodiment of the invention, silica, coal of oil shale hydrocarbons, and fluorspar or fluorosalt residues from oil shale wastes, are loaded into a column reactor that is heated and provided with a supply of vaporous sulfuric acid. The following reaction occurs.

$$H_2SO_4+C+SiO_2+CaF_2\rightarrow CaSO_4+\text{Compound} \\ \text{II}+\text{Compound III}+CO \quad \text{Equation 2}$$

By-products of the above noted reactions include valuable ethylene, acetylene, and miscellaneous other gaseous species. The by-product gases are preferably recirculated back to the reaction column while the desired ESCTF is extracted by condensations.

DETAILED DESCRIPTION OF THE INVENTION

Figure 1:
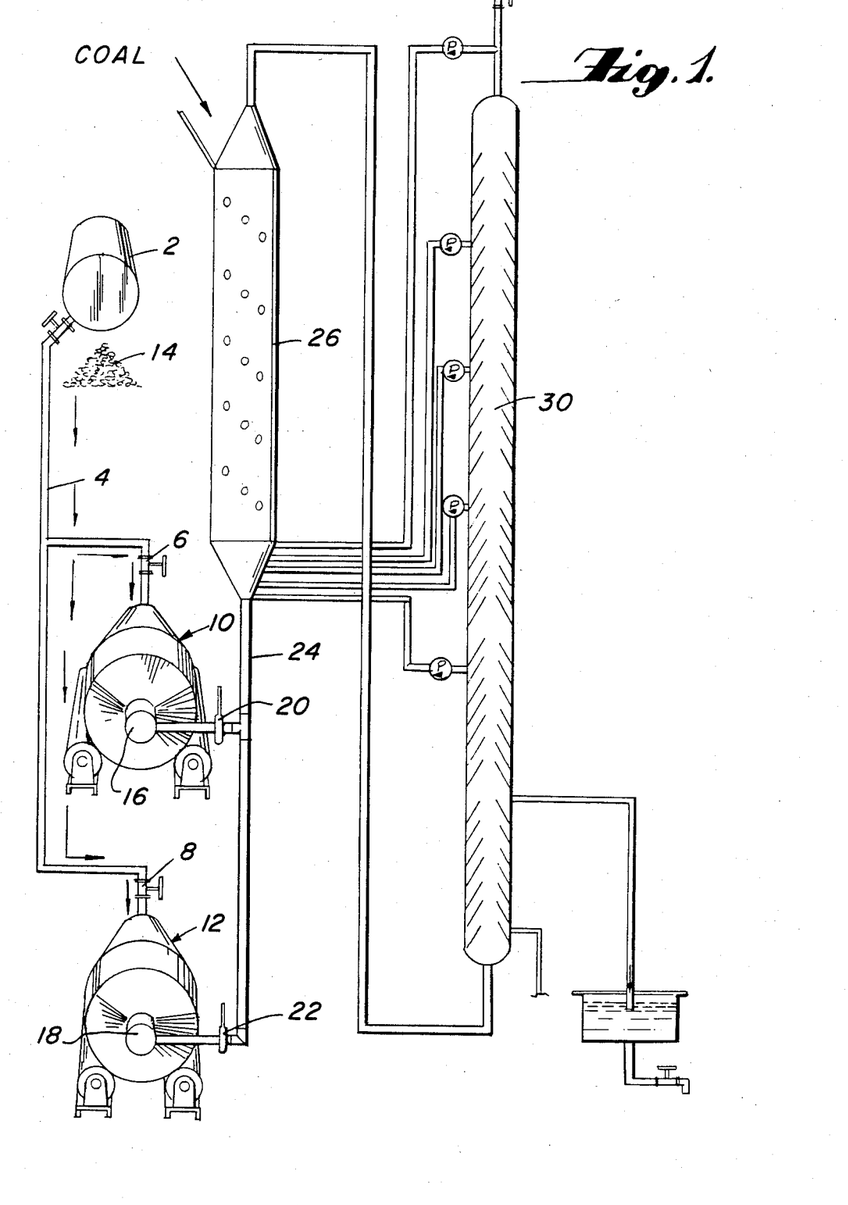
FIG. 1 shows schematically one form of apparatus employed to make the monomers of the invention.

Referring now more particularly to FIG. 1 of the drawings, 98% sulfuric acid (H$_2$SO$_4$) or oleum (H$_2$S$_2$O$_7$) stored in Vessel 2 is piped through conduit 4 to valves 6 and 8 to intermittently enter rotary mills 10 and 12. Feed stock 14, a mixture of approximately 28% silica and 72% fluorspar is also intermittently added to rotary mills 10 and 12.

Rotary mills 10 and 12 are preferably constructed of mild steel and are lined with fluoropolymer resin such as polytetrafluoroethylene, ethylene tetrafluoroethylene copolymer, ethylene chlorotrifluoroethylene copolymer, or perfluoroethylenepropylene copolymer. Mills 10 and 12 are equipped with heat sources, preferably producer gas type burners to use excess combustible gases generated as a by-product of the invention in reactor 26.

Mills 10 and 12 are also preferably charged with fluoropolymer coated steel balls that serve as mixing and pulverizing agents when carried up and dropped by usual ball mill type internal features within 10 and 12. Sulfuric acid, silica, and fluorspar feedstocks are thus milled together to cause continuous chemical reaction and nearly complete release of available fluorine as silicon tetrafluoride gas. The released silicon tetrafluoride gas is vented out of mills 10 and 12 through blowers 16 and 18 intermittently past valves 20 and 22 and into conduit 24. The solid residues of calcium sulfate produced in mills 10 and 12 are countercurrently dumped past fresh feedstocks as heat is regeneratively exchanged.

It is preferred to control the output of each mill by adjustments of the temperature and rates of rotation and to valve off mills being cleaned and recharged by valves 20 and 22. Thus a more or less continuous flow of silicon tetrafluoride can be maintained in conduit 24 for delivery to reactor 26.

Reactor 26 is preferably a superalloy tubular column provided with heaters. The heaters are preferably burners of the natural gas type for burning excess combustible gases produced by the invention. In operation reactor 26 is loaded with coal or charcoal or other suitable carbon sources such as coke. Valves 20 and 22 are closed while the carbon bed is heated to accomplish out gasing of volatiles and to develop sufficient preheat to accomplish the objects of the invention. The overall reactions accomplished are as follows:

EQUATION 3

EQUATION 4

$$SiF_4 + CH_4 + 2C \longrightarrow \text{Compound II} + \text{Compound III} +$$
$$(H_2 + C_2H_2 + C_2H_4 + CO)$$

In EQUATION 3, two molecules of water are actually produced for each molecule of silicon tetrafluoride. Some of this water stays with the calcium sulfate as a water of hydration. Some of the water is used to react with incoming oleum to form sulfuric acid. The remaining portion of the water may be scrubbed from the silicon tetrafluoride by a suitable dessicant, preferably concentrated sulfuric acid, or it may be allowed to enter reactor 26 and undergo water-gas reactions with the heated carbon to produce hydrogen and carbon monoxide.

$$C + H_2O \rightarrow CO + H_2 \quad \text{EQUATION 5}$$

The carbon monoxide and hydrogen released by the reaction of EQUATION 5 along with acetylene, ethylene, and other gaseous combustants are available from condensor tower 30 for burning as a fuel to heat reactor 26 or mills 10 and 12. During periods when sufficient heat is available in reactor 26 and mills 10 and 12, the combustible gases shown in parenthesis in EQUATION 4 are recycled to reactor 26 along with silicon-carbon-tetrafluoride and any unreacted silicon tetrafluoride to produce ethylene-silicon-carbide-tetrafluoride (ESCTF).

EQUATION 6

Compound II + Compound III

The desired silicon carbide tetrafluoride is separated as a liquid from the other gaseous constituents by condenser tower 30 and is stored in reservoir 32.

In plant locations proximate to phosphate fertilizer production operations it is preferred to take waste silicon tetrafluoride through pressurizing blowers and then to operate according to EQUATION 4. Pressurized waste silicon tetrafluoride and methane flows into carbon filled reactor 26 and ESCTF is produced. Depending upon the purity of the waste silicon tetrafluoride feedstock: hydrogen, carbon monoxide, acetylene, ethylene, and other compounds may be produced by reactions illustrated in EQUATION 4 and 5.

Combustible compounds such as carbon monoxide, hydrogen, acetylene, and ethylene may be burned to provide heat for mills 10 and 12 or reactor 26. In those instances where high hydrogen to carbon ratio by-products are produced, considerable methane may be withheld in EQUATION 4. The hydrogen and hydrogenous by-products may be recirculated to reactor 26 along with any silicon-carbide-tetrafluoride and incoming silicon tetrafluoride to produce ethylene-silicon-carbide tetrafluoride.

ti $\quad C+H_2+C_2H_2+SiF_4+SiCF_4 \rightarrow \text{Compound II}+$ Compound III $\quad$ EQUATION 7

Significant advantages of the invention over previous methods to produce fluorochemicals are demonstrated by the economics offered through use of a waste silicon tetrafluoride feedstock along with plentiful coal and natural gas. Another important aspect is the ability to use relatively broad tolerances of feedstock chemistries, through recycling and useful combustion of gasified coal by-products.

Due to environmental control pressures, many sulfur bearing mineral extraction operations that formerly released oxides of sulfur to the atmosphere now produce large excesses of sulfuric acid. Another aspect of the present invention is production of ethylene-silicon-carbide-tetrafluoride (ESCTF) by reactions involving sulfuric acid, a carbon source, silica, and fluorspar. This method is preferred in instances where natural gas is not readily available or where there are insufficient water supplies for flotation separation of calcium fluoride from silicon oxides in otherwise useful ores. EQUATION 8 illustrates the overall reaction.

$$H_2SO_4 + C + SiO_2 + CaF_2 \rightarrow CaSO_4 + \text{Compound}$$
$$\text{II} + \text{Compound III} + CO \quad \text{EQUATION 8}$$

In this embodiment, reactor 26 is loaded with a mixture having approximately the following weight proportions.

60 TONS COAL

216 TONS: 72% $CaF_2$, 28% $SiO_2$ Ore

Preferably the coal and fluorspar ore are at minus 14 mesh or finer particle sizes and are intimately mixed prior to loading into reactor 26. Mills 10 and 12 or a variety of other suitable designs may be employed for this purpose. The mixture of coal and fluorspar loaded into 26 is preheated to approximately 1,000° F. and then subjected to a flow of hot sulfuric acid fumes to cause reactions according to EQUATION 8. ESCTF produced is separated as a liquid from carbon monoxide and other vaporous products by condenser 30. The carbon monoxide and other combustible gases may be burned to heat reactor 30. Solid compounds, including unreacted silicon dioxide, calcium sulfate, and entrained coal particles are intermittently cleaned from reactor 26 to make room for new charges of feedstocks. It is preferred to dump exiting charges into a counter current heat exchanger through which sulfuric acid traveling toward reactor 26 is routed for purposes of heat recovery.

It is again emphasize that the invention provides a practical means for gasifying coal to monomers such as $SiF_2=CF_2$, $CF_2=CF_2$, and ESCTF through the use of widespread, inexpensive reactants. The ESCTF is particularly desirable as a starting stock for thermoplastic polymers, fluoroliquids, and fluorogases. As a high molecular weight polymer, ESCTF offers attractive thermophysical properties.

Figure 2:
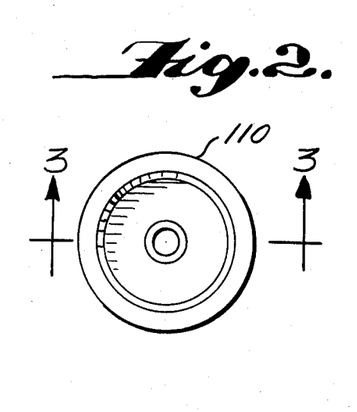
FIG. 2 is a side elevational view of a plastic pipe end heating member coated with the organosilicon polymer of the present invention.
Figure 3:
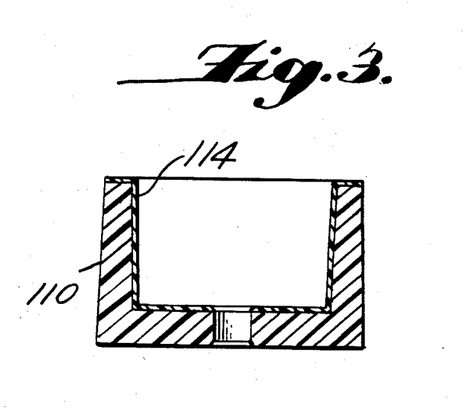
FIG. 3 is a cross-sectional view taken along the line 3—3 of FIG. 2.
Figure 4:
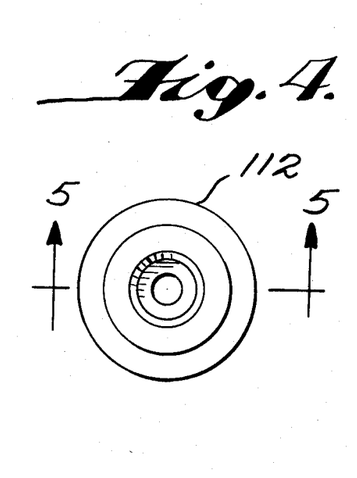
FIG. 4 is a side elevational view of a plastic fitting socket heating member coated with the organosilicon polymer of the present invention.
Figure 5:
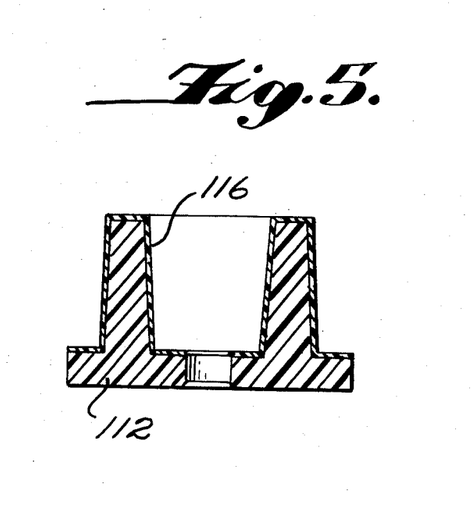
FIG. 5 is a cross-sectional view taken along the line 5—5 of FIG. 4.

Referring now more particularly to FIGS. 2–5 of the drawings, there is shown therein a preferred exemplary embodiment of the use of the organosilicon polymer as a coating. FIGS. 2 and 3 illustrate a socket member 110 formed of a suitable plastic material. Member 110 may also be formed of metal, sintered metal serving as a particular good base material to receive a coating thereon. FIGS. 4 and 5 illustrate a comparable sized plug number 112 which also can be used as a smaller sized socket member. The socket and plug members 110 and 112 constitute one pair of a set of pairs of different diameter sizes for use in heating a plastic pipe end, e.g. of polyethylene or polyvinyl chloride or Delrin, and a socket of a plastic fitting, e.g. of polyethylene or polyvinyl chloride or Delrin, in order to effect a fusion welding joint between the pipe and fitting.

In operation, the members 110 and 112 are mounted in axially aligned relation on opposite sides of a heating platten member of a heating device so that they can be brought up to a desired operating pressure. After they have been properly brought up to operative temperature levels, the pipe end is engaged within the socket member 110 and the socket of the fitting is engaged over the plug member. After being subjected to the heat for a predetermined period (e.g. 10 seconds) the pipe and fitting are removed from the members 110 and 112 and interengaged to effect the fusion welded joint.

Apparatus for accomplishing the above fusion welding technique with members 110 and 112 is disclosed in my application Ser. No. (Dkt. 54) filed concurrently herewith, the disclosure of which is hereby incorporated by reference into the present specification.

For present purpose it is sufficient to state that at least the surfaces of the members 110 and 112 which are contacted by the plastic pipe end or the socket of the plastic fitting are coated with the organosilicon polymer of the present invention as indicated at 114 in FIGS. 2 and 3 and at 116 in FIGS. 4 and 5.

EXAMPLE 1

Ten pounds of phosphate rock containing 31% $P_2O_5$, 49% CaO, 1.2% $Al_2O_3$, 1% $Fe_2O_3$, 8.5% $SiO_2$, 2.5% $SO_3$, 3.8% F, are ball milled to 100% minus 100 mesh and then heated to approximately 300° F. in a Teflon lined ball mill having Teflon covered steel balls. During continuous rotation at 300° F., 6.7 pounds of 98% pure sulfuric acid are added over the period of approximately 30 minutes. Gaseous products evolved from the reaction are scrubbed in 98% sulfuric acid at room temperature. Approximately 0.3 pounds of silicon tetrafluoride are recovered from the scrubbed gas flow and added to 0.005 lbs methane gas. The mixture of silicon tetrafluoride and methane gas is then added under more or less constant flow conditions to a ¾" diameter type 310 stainless steel tube about 36" long packed with granulated coal and having the middle section of approximately 20 inches heated in a tubular furnace to about 1,500° F. An output of about 15% ESCTF ($SiC_3F_4H_4$) gas in a mixture of $SiF_4$, $CH_4$, $C_2H_2$ and other gaseous products is obtained. Recycling the produced gas mixture or decreasing the rate of flow of the silicon tetrafluoride and methane mixture into the granulated coal packed reaction tube increases the yield of ESCTF ($SiC_3F_4H_4$). The solids left after reaction in the heated ball mill were compared to normal superphosphate marketed for fertilizer and found to contain about equal amounts of $P_2O_5$ based upon citrate solubility. The ESCTF can be recovered from the gaseous mixture as indicated above by cooling the gaseous mixture to condensed the ESCTF and then the liquid can be further purified by distillation.

EXAMPLE 2

Ten pounds of acid grade fluorspar, four pounds of silica, and four pounds of coal are ball milled together to produce a minus 60 mesh mixture. A sufficient quantity of this mixture is added to a ¾" diameter 36" long reactor tube of type 310 stainless steel to pack fully. One end of the reactor tube is connected to a heated supply of 98% pur sulfuric acid and the other to a room temperature scrubber bath of sulfuric acid. The middle 20" section of the reactor tube is heated in a tube furnace to approximately 1,500° F. The heated supply of sulfuric acid is vaporized into the reaction tube until the sulfuric acid scrubber ceases to have a gaseous output. Product gases from the crubber are approximately 20% ESCTF ($SiC_3F_4H_4$) in a mixture with CO, HF, $SiF_4$, $CO_2$ and $H_2S$. The ESCTF can be separated out by condensing at a temperature below room temperature.

EXAMPLE 3

A fluorspar ore containing approximately 19% $SiO_2$, 78% $CaF_2$, 1% $CaCO_3$, 1% $Al_2O_3$, and 1% other minerals is ball milled to minus 100 mesh and ten parts of this ore is dried and transferred to a Teflon lined ball mill and heated to 350° F. Then parts of concentrated 98% pure sulfuric acid is added to the heated ore. Gaseous outputs from the reaction between the sulfuric acid and the ore consist essentially of silicon tetrafluoride, hydrogen fluoride and water vapor. Increasing the temperature of the Teflon lined ball mill increases the yield of water vapor. Decreasing the temperature of the Teflon line ball mill decreases the output of water vapor but has little effect upon the output of silicon tetrafluoride or hydrogen fluoride.

Gaseous products of the Teflon ball mill are separated by passage through the inner tube of a heat exchanger consisting of a coaxial steel tube with the outer tube flowing a coolant. Hydrogen fluoride is condensed at 67° F. leaving silicon tetrafluoride to pass on as a gas. Hydrogen fluoride is stored at dry ice temperatures in polyolefin canisters. The silicon tetrafluoride along with equal molar parts of $CH_4$ is passed on to a column of −14 mesh coal granules heated to about 1,800° F. within a 36" long type 310 stainless steel tube. Ethylene-silicon-carbide tetrafluoride (ESCTF) is produced as in Example 1 above. Increased yields of ESCTF are produced when ethylene gas is substituted for $CH_4$ indicating that the desired product is partially limited by the availability of ethylene production.

EXAMPLE 4

Carbon is dissolved in carbon disulfide to produce a fully saturated solution of about 200 weight parts. The carbon saturated solution is transferred to a 5,000 psi Teflon lined reaction bomb. Ten parts minus 200 mesh $SiO_2$, twenty-six parts minus 200 mesh $CaF_2$ and finally seventeen parts $H_2SO_4$ are added to the Teflon lined reactor. The sealed reactor bomb is ultrasonically agitated for twenty-four hours while the temperature is held at about 80° F. in a bath of water. Gaseous products including silicon carbide tetrafluoride, $SiCF_4$, and silicon tetrafluoride, $SiF_4$, are produced in amounts indicating more than 30% release of fluorine from the original change of calcium fluoride.

The gaseous products are added to a ¾" diameter; 0.020 Wall, 36" long, type 310 stainless steel tube filled with −14 mesh coal granules heated to about 2,000° F. throughout the center 20" by a horizontal tube furnace.

The original ratio of 40% SiCF$_4$ is shifted to 55% SiCF$_4$ and 45% SiF$_4$. The SiCF$_4$ can be recovered in liquid form by condensing at below room temperature.

EXAMPLE 5

A mixture of SiF$_4$ and SiCF$_4$ gases are prepared as in Example 4. Weight parts of ethylene gas equal to the amount of SiCF$_4$ are mixed with the bomb gases and circulated to the coal filled stainless steel reactor tube as in Example 4. The yield of gases out of the stainless reactor tube is approximately 75% ESCTF (SiC$_3$F$_4$H$_4$).

EXAMPLE 6

In this example there was employed a concrete mixer type mixing drum.

The outer end of the drum is connected to a screw extruder to extrude reaction product residues and support countercurrent heat exchange to the incoming change flows of mixed fluoride and silica powders (and optionally also coal powder).

The mixing drum is loaded and operated at an average charge of about 4½ tons of ingredients while being heated to about 350° F. and while being rotated at about 15 revolutions per minute. About 12 tons of solid residues mostly CaSO$_4$, at about 125° to 180° F. are expelled per hour. The input screw extruder is operated at about 18 revolutions per minute, and provides about 9 tons of 27% to 30% SiO$_2$ and 70% to 73% CaF$_2$ powders to the drum. H$_2$S$_2$O$_7$ liquid is added through the bore of the input screw extruder at a rate of about 7.5 tons per hour. Combustion gases and excess air enter the drum at 350° F. to 400° F. and are exhausted at about 170° to 210° F. SiF$_4$ is extracted from the drum at about 4.3 tons per hour.

Production of ESCTF may occur by several mechanisms. The reactions that produce ESCTF are envisioned as follows although the invention is not limited by such theory of reaction.

EQUATION 9

EQUATION 10

EQUATION 11

Ziegler-Natta catalysts suitable for ethylene, vinylidene halide, and vinyl halide polymerization are effective for polymerizing ESCTF (SiC$_3$F$_4$H$_4$). Similarly, the polymer may be prepared in the presence of water and initiators that provide olefin polymerization.

Because of the similarity in free energy of polymerization to ethylene-tetrafluoroethylene and ethylene-chlorotrifluoroethylene, ESCTF can be processed in essentially the same apparatus and achieve about the same process performance.

The process can comprise, consist essentially of or consist of the steps set forth with the recited materials.

Example 4 illustrates a novel method of reaction where carbon in solution is reacted to form SiCF$_4$.

In forming ESCTF and analogues thereof the source of carbon can be coal, carbon or a lower aliphatic hydrocarbon such as methane, ethane, ethylene, acetylene.

Illustrative polymerization examples are set forth below.

EXAMPLE 7

A 100' length of ½" O.D., 0.035 wall, type 316 stainless steel tube is formed into a helical coil to develop a cylindrical form about 10" in diameter and about 45" in height. This coil is attached with tube fittings for circulation with a cylindrical loading and instrumentation vessel measuring about 7" in diameter and 20" in height with ½" walls. Circulation is provided by a magnetic drive to a small hermetically sealed turbine pump between the bottom of the loading cylinder and the circulation coil. Temperature control is provided by immersion of the circulation coil in an open bath of water maintained at constant temperature. Blow-out safety is provided by a rupture disc vented the roof and sewer. Inert mediums such as water are used to circulate and thermally stabilize the polymerization reaction. Polymerization of SiCF$_4$ is accomplished by (1) evacuating the loading vessel; (2) charging the loading vessel with liquid monomer cooled by a liquid nitrogen heat sink during distillation and collection; (3) adding sufficient water with a high pressure positive displacement pump and then circulating the reactor contents through the water bath heat source to stabilize the contents at about 70° C. and 1500 psig pressure; (4) adding about 0.1% of benzoyl peroxide per weight of monomer as a catalyst; (5) adding about 2% ethylene per weight of monomer; (6) circulation until polymerization is complete as evidenced by pressure drop. Polymerized powder removed from the reactor is placed on a 450° C. stainless steel platten to produce a resinous mass which is immediately transferred and pressed to a clear film between massive polished aluminum plattens. Clear films of 0.006" to 0.010" thickness transmit about 91% to 95% of the solar spectrum and show no loss of solar transmissivity, and no significant loss of ductility after accelerated exposure to ultra violet radiation between 0.25 and 0.38 microns wavelength amounting to the equivalent of about 20 years of solar exposure.

EXAMPLE 8

100 parts of SiCF$_4$ and 25 parts of ethylene are added to the reactor described above in Example 7. Distilled water is added to pressurize the reactor to 1500 psig. 0.125 parts of benzoyl peroxide are added and the contents are circulated through a 70° C. water bath until the pressure drops to about 250 psig. The contents are filtered and dried. The dried filter cake is fused on a 450° C. platten and immediately transferred and pressed to 0.006" to 0.010" thickness. The clear film transmits about 92% to 98% of the solar spectrum and shows no loss of transmissivity or loss of ductility after accelerated exposure to ultra violet radiation between 0.25 and 0.38 microns wavelength amounting to the equivalent of about 20 years of solar exposure.

EXAMPLE 9

100 parts of SiCF$_4$ and 25 parts of ethylene are added to the reactor described in Example 7. Sufficient n-pentane is added to pressurize the reactor to 500 psig. 0.10 parts —250 mesh chromic oxide particles are added and the system is circulated through the heat exchange coil to achieve a temperature of about 95° C. from hot water in the open bath. Polymerization is continued until the pressure drops to about 50 psig. The contents are filtered and dried. The dried filter cake is fused on a 450° C. platten and immediately transferred and pressed to 0.006" to 0.010" thickness. The clear film transmits about 92% to 98% of the solar spectrum and shows no loss of transmissivity or loss of ductility after accelerated exposure to ultra violet radiation between 0.25 and 0.38 microns wavelength amounting to the equivalent of about 20 years of solar exposure.

EXAMPLE 10

100 parts of $SiCF_4$ and 47 parts of ethylene are added to the reactor described in Example 7. Sufficient n-pentane is added to pressurize the reactor to 150 psig. 0.10 parts chromia alumina spinel in $-250$ mesh particles are added and the contents are circulated at about 90° C. for 24 hours using heated water in the open bath to maintain the temperature of the polymerization charge. The reactor contents are drained and filtered. The filtrate is dried and fused on a 450° C. platten and immediately transferred and pressed to a 0.006 to 0.010 film thickness between polished aluminum plates. The clear film transmits about 92% to 95% of the solar spectrum and shows essentially no loss of ductility after accelerated exposure to ultra violet radiation between 0.25 and 0.38 microns wavelength amounting to about 20 years of Phoenix area solar exposure.

EXAMPLE 11

156 parts of acid grade, $-320$ mesh fluorspar ($CaF_2$) and 44 parts of $-250$ mesh silica ($SiO_2$) are placed in a rotary mild steel reactor. The reactor is a modified concrete mixer equipped with a natural gas heater and a gas tight cap. The dry charge of fluorspar and silica is preheated to about 350° F. while evolved gases including air and water vapor are valved to a vacuum roughing pump. 215 parts of dry sulfuric acid ($H_2SO_4$) are added and the reactor is heated to about 375° F. Evolved $SiF_4$ is displaced through a rotary union to a preheated monomer synthesizer consisting of a type 310 stainless steel pipe packed with metallurgical coke and preheated to about 1900° F. Condensable gases evolved from the monomer synthesizer are trapped in a cryogenic collector that is cooled by liquid nitrogen. Partial warming of the condensed gases allows boil-off of higher vapor pressure $SiF_4$ and $CF_4$ while lower vapor pressure $SiCF_4$ is retained. 100 parts $SiCF_4$, 6 parts propylene, 1 part vinyl chloride and 0.5 parts diisopropyl peroxydicarbonate (IPP) are added to 160 parts distilled water in the polymerization reactor described above. Pressure is controlled at about 130 psig as the circulated reaction mixture is elevated to about 55° C. After approximately 24 hours of circulation the contents are filtered and the solids are dried and fused on a 450° C. hot plate. Fused resins are immediately transferred and pressed between polished aluminum plates to form a clear 0.006" to 0.010" film.

This clear film transmits about 92% to 98% of the solar spectrum and shows essentially no loss of transmissivity of ductility when exposed to accelerated ultra violet radiation counts amounting to about 20 years exposure to the sun.

EXAMPLE 12

100 parts $SiCF_4$ prepared by the above described process, 65 parts vinyl chloride ($C_2H_3Cl$), 0.75 parts IPP and 200 parts distilled water are charged into the polymerization reactor described above. Pressure is controlled at about 130 psig as the circulated mixture is elevated to bout 55° C. After about 24 hours of circulation the contents are filtered and the solids are dried and fused on a 450° C. hot plate. Fused resins are immediately transferred and pressed between polished aluminum plates to form a clear 0.006" to 0.010" film. The clear film transmits more than 90% of the solar spectrum and shows practically no loss of ductility or loss of transmissivity upon accelerated exposure to U.V. photon counts amounting to the equivalent of 20 years real time exposure to the sun at Phoenix, Ariz.

EXAMPLE 13

100 parts of the dried particulate material produced according to Example 8 is loaded into the reactor described above and evacuated with a vacuum pump.

Sixty parts silica, one hundred sixty parts acid grade fluorspar, and one hundred parts metallurgical coke are mixed and used to fill a 3" dia $\times$ 0.125" wall, 12" long horizontal tube of type 416 stainless steel. The horizontal tube and dry charge are placed in a horizontal tube furnace and heated to about 850° C. with continuous purging using natural gas to displace air and other outgassed atmospheres. Over a ten minute period, 180 parts oleum ($H_2S_2O_7$) and 10 parts natural gas are fed into the inlet of the reactor tube. Evolved gases are filtered through copper turnings and condensable vapors are collected in a liquid nitrogen cooled trap. Higher boiling point compounds are allowed to boil off of the collected condensate and 100 parts $SiC_3H_4F_4$ (ESCTF) is then boiled-off to the reactor described above. $SiC_3H_4F_4$ vapors are circulated through the particulate charge contained by 400 $\times$ 400 mesh screens within the canister chamber of the reactor. The contents are heated to approximately 175° C. by transfer to the vapors circulating in the tube coil from hot silicone oil in the bath. Circulation is continued for approximately 24 hours starting at about 500 psig system pressure. Polymerized particulate material deposited upon the seed charge amounting to about 140 parts are recovered from the canister chamber and fused on a 450° C. hot plate and then immediately transferred and pressed to a 0.006" thick film. The clear film transmits more than 90% of the solar spectrum and shows no loss of transmissivity or loss of ductility after accelerated exposure to ultra violet radiation between 0.25 and 0.38 microns wavelength amounting to the equivalent of about 20 years of solar exposure.

In the examples above of polymerization of the novel silicon compounds are used in an amount of 50% or more of the polymerizable materials.

In making copolymers it is possible to employ for example 10 to 90 mole % of the novel silicon containing monomer and 90 to 10 mole percent of copolymerizable monomer or monomers.

For making non-stick coatings, e.g. coatings on a socket member and plug member for welding a plastic pipe end to a fitting it has been found preferable to use the polymer as soon as possible after it is formed. Also it has been found desirable for non-stick coating to have an alternating structure in copolymers, e.g. a 1:1 mole ratio of tetrafluoroethylene or other copolymerizable monomer to perfluorovinyl perfluorosilyl ether. The use of a copolymerizable monomer in general has been found to be advantageous because it imparts to toughness and quits a preferred milky precipitate for coating purposes. The orgonosilicon homopolymer are more shear sensitive to form strings and gobs.

EXAMPLE 14

One stream of silicon tetrafluoride produced by reacting 200 parts of sulfuric acid with 60 parts silica and 150 parts calcium fluoride is reacted with low ash coke packed in a one inch diameter type 310 stainless steel tube that is maintained at 1,500° F. for about the first six feed of a 60 foot long helical coil. Carbon tetrafluoride ($CF_4$) and fluorinated ethylene ($C_2F_4$) are the principal compounds produced by the reaction. A second stream of 100 parts silicon tetrafluoride produced by the same reaction of sulfuric acid, silica, and calcium fluoride is mixed with sixteen parts oxygen and reacted with low ash coke packed in a second one inch diameter type 310 stainless steel tube that is maintained at 1,500° F. for about the first twenty feet of a 100 foot long helical coil. Significant amounts of $C_2SiOF_6$ produced by the reaction in the second coil and separated using liquid nitrogen as a coolant in the condenser as pointed out supra, are extracted along with carbon tetrafluoride and fluorinated ethylene from the first packed tube reactor by a water jet extractor which feeds a six-stage turbine pump with a variable rate of recirculation.

Polymerization of fluorinated ethylene and occurs in the water and produces a milky solution. Following separation of the milky solids from the water in a centrifuge, the solids are dried and pressed at 650° F. to form a consolidated thermoplastic that is transparent and extremely resistant to chemical attack. The formula for the new thermoplastic is $(C_2F_4)_o$ $(C_2SiOF_6)_p$ where o may be less than p, equal to p, or far exceed p depending upon the relative amounts of products from each of the two reactor tubes. As stated supra preferably o is equal to p if the copolymer is to be used as a non-stick coating. The ratio of tetrafluoroethylene to perfluorovinyl trifluorsilyl ether is controlled, e.g. to 1:1 on a mole basis by regulating the amount of material from the first coil mixed with the material from the second coil.

EXAMPLE 15

In the procedure described in Example 14, fractionation of the reactor products was utilized to separate another compound $C_3SiOF_8$ (by regulating the flow of liquid nitrogen). This was polymerized by the aqueous dispersion technique described to form a milky solution.

The milky solution was spray deposited upon aluminum bodies including strips about 1″ wide and 6″ long which were baked for one hour at 300° F. then for twenty minutes at 800° F. Both grit blasting and anodizing of the aluminum was tested and found to be suitable surface preparations in order to produce adherent coatings of solid $(C_3SiOF_8)_p$. The coatings were tested in making pipe welds for abrasion resistance and release properties using fused polyolefins such as polyethylene, polypropylene, polybutylene, and poly-4-methylpentene as the pipe at temperatures up to about 600° F. The coatings were satisfactory in both abrasion and release properties with these polymers.

EXAMPLE 16

The techniques described in Examples 14 and 15 were used to prepare a copolymer of ($C_2SiOF_6$) and ($C_2F_4$) in about a 1 to 1 ratio of "p" to "o". When tested as indicated in Example 15 as a coating for abrasion and release properties this material was found to be superior to teflon materials such as PFA (perfluoroalkoxy polymer) and TFE (polytetrafluoroethylene) for abrasion and release capabilities.

EXAMPLE 17

The techniques described in Example 16 were used to prepare a polymer coating consisting of a copolymer of $(C_2H_2F_2)_o$ (vinylidene fluoride) and $(C_2SiOF_6)_p$ in the ratio of about 1 to 1 of "o" to "p". When tested for abrasion and release properties this material was found to have better abrasion resistance than the polymer of Example 16 but reduced release capabilities compared to the polymer of Example 16.

EXAMPLE 18

The techniques described in Example 16 were used to prepare a polymer coating consisting of a copolymer of $(C_2F_3Cl)_o$ (chlorotrifluoroethylene) and $(C_2SiOF_6)_p$ in about equal molecular percentages. When tested for abrasion and release characteristics it was found to rank between the copolymers of Example 17 and Example 16.

EXAMPLE 19

The techniques described in Example 16 were used to prepare a polymer coating consisting of a copolymer of $C_2H_2F_2$ and $C_3SiOF_8$ in about equal molecular percentages. When tested for abrasion resistance and release properties this material was found to be about equal to the material of Example 17.

EXAMPLE 20

The techniques of Example 16 were used to prepare a copolymer coating of $(CF_2.CF.CF_3)_o$ and $(C_3SiOF_8)_p$ in about equal molecular percentages. When tested for abrasion resistance and release properties this material was found to be more abrasion resistant than the material of Example 19 and capable of withstanding equal abrasion at higher temperatures than the material of Example 19. The release properties were about equal to the material of Example 15.

What is claimed is:

1. A fluorine containing compound which has the formula where m is 0 or 1.

2. A fluorine containing compound according to claim 1 which has the empirical formula $C_2SiOF_6$.

3. A fluorine containing compound according to claim 1 which has the empirical formula $C_3SiOF_8$.

4. A polymer of the monomer of claim 1.

5. A polymer according to claim 4 wherein the fluorine containing compound has the empirical formula $C_2SiOF_6$.

6. A polymer according to claim 5 which is a homopolymer.

7. A polymer according to claim 6 which is a copolymer with a copolymerizable monomer.

8. A polymer according to claim 7 wherein the copolymerizable monomer is present in about an equimolar amount to the $C_2SiOF_6$.

9. A polymer according to claim 8 wherein the copolymerizable monomer is ethylene, propylene, vinyl chloride, tetrafluoroethylene, perfluoroethylene, vinyl fluoride, vinylidine fluoride or chlorotrifluoroethylene.

10. A polymer according to claim 9 wherein the copolymerizable monomer is fluorine containing monomer.

11. A polymer according to claim 10 wherein the copolymerizable monomer is tetrafluoroethylene.

* * * * *